US011807870B2

(12) United States Patent
Feyeux et al.

(10) Patent No.: US 11,807,870 B2
(45) Date of Patent: Nov. 7, 2023

(54) CELLULAR MICROCOMPARTMENT AND PREPARATION PROCESSES

(71) Applicants: UNIVERSITE DE BORDEAUX, Bordeaux (FR); CENTRE NATIONAL DE LA RECHERCHE SCIENTIFIQUE, Paris (FR); INSTITUT D'OPTIQUE THEORIQUE ET APPLIQUEE, Palaiseau (FR)

(72) Inventors: Maxime Feyeux, Talence (FR); Kevin Alessandri, Bordeaux (FR); Pierre Nassoy, Bordeaux (FR); Laurent Cognet, Bordeaux (FR); Gaëlle Recher, Talence (FR); Erwan Bezard, Bordeaux (FR)

(73) Assignees: UNIVERSITE DE BORDEAUX, Bordeaux (FR); CENTRE NATIONAL DE LA RECHERCHE SCIENTIFIQUE, Paris (FR); INSTITUT D'OPTIQUE THEORIQUE ET APPLIQUEE, Palaiseau (FR)

( * ) Notice: Subject to any disclaimer, the term of this patent is extended or adjusted under 35 U.S.C. 154(b) by 577 days.

(21) Appl. No.: 16/462,962

(22) PCT Filed: Nov. 23, 2017

(86) PCT No.: PCT/FR2017/053225
§ 371 (c)(1),
(2) Date: May 22, 2019

(87) PCT Pub. No.: WO2018/096277
PCT Pub. Date: May 31, 2018

(65) Prior Publication Data
US 2019/0330589 A1 Oct. 31, 2019

(30) Foreign Application Priority Data
Nov. 23, 2016 (FR) ...................................... 1661377

(51) Int. Cl.
| | | |
|---|---|---|
| C12N 5/00 | (2006.01) | |
| C12M 1/00 | (2006.01) | |
| C12M 1/12 | (2006.01) | |
| C12N 5/074 | (2010.01) | |

(52) U.S. Cl.
CPC .......... *C12N 5/0075* (2013.01); *C12M 23/20* (2013.01); *C12M 25/01* (2013.01); *C12M 25/16* (2013.01); *C12N 5/0012* (2013.01); *C12N 5/0696* (2013.01); *C12N 2501/727* (2013.01); *C12N 2513/00* (2013.01); *C12N 2533/74* (2013.01); *C12N 2533/90* (2013.01); *C12N 2535/00* (2013.01)

(58) Field of Classification Search
CPC .. C12N 5/0075; C12N 5/0012; C12N 5/0696; C12N 2501/727; C12N 2513/00; C12N 2533/74; C12N 2533/90; C12N 2535/00; C12M 23/20; C12M 25/01; C12M 25/16
See application file for complete search history.

(56) References Cited

U.S. PATENT DOCUMENTS

| | | | | |
|---|---|---|---|---|
| 2014/0127290 A1* | 5/2014 | He | .......................... | C12N 11/04 424/451 |
| 2015/0017676 A1* | 1/2015 | Bibette | .................... | B01J 13/08 435/174 |
| 2015/0132847 A1 | 5/2015 | Lipke et al. | | |
| 2016/0068385 A1* | 3/2016 | Chen | ................... | B81C 1/00119 422/503 |
| 2020/0063099 A1 | 2/2020 | Feyeux et al. | | |

FOREIGN PATENT DOCUMENTS

| | | |
|---|---|---|
| WO | WO 2016/141137 | 9/2016 |
| WO | WO 2018/096278 | 5/2018 |

OTHER PUBLICATIONS

Ashida et al ("Propagation of human iPS cells in alginate-based microcapsules prepared using reactions catalyzed by horseradish peroxidase and catalase," Artifical Cells, Nanomedicine and Biotechnology, 1-4, Nov. 16, 2015).*
Taniguchi et al ("Lumen Formation is an intrinsic property of isolated human pluripotent stem cells," Stem Cell Reports, vol. 5, 954-962, Dec. 8, 2015).*
Ikeda et al ("3D culture of mouse IPSCS in hydrogel core-shell microfibers," MEMS 2015, Estoril, Portugal, Jan. 18-22, 2015).*
Beers et al ("Passaging and colony expansion of human pluripotent stem cells by enzyme-free dissociation in chemically defined culture condition," Nature Protocols, vol. 7, No. 11, 2012).*
Alessandri et al ("A 3D printed microfluidic device for production of functionalized hydrogel microcapsules for culture and differentiation of human Neuronal Stem Cells (hNSC)," Lab Chip, 2016, 16, 1593-1604).*
Wang et al ("Mixed hydrogel bead-based tumor spheroid formation and anticancer drug testing," Analyst, 2014, 139, 2449-2458) (Year: 2014).*
Hunt, N. C. et al. "3D culture of human pluripotent stem cells in RGD-alginate hydrogel improves retinal tissue development" *Acta Biomaterialia*, 2017, pp. 329-343, vol. 49.
Song, W. et al. "Engraftment of human induced pluripotent stem cell-derived hepatocytes in immunocompetent mice via 3D co-aggregation and encapsulation" *Scientific Reports*, Nov. 23, 2015, pp. 1-13, vol. 5, No. 1.

(Continued)

*Primary Examiner* — Anoop K Singh
*Assistant Examiner* — Suzanne E Ziska
(74) *Attorney, Agent, or Firm* — Greer, Burns & Crain, Ltd.

(57) ABSTRACT

The invention relates to a cellular microcompartment comprising successively, organized around a lumen, at least one layer of pluripotent cells, an extracellular matrix layer and an outer hydrogel layer. The invention also relates to processes for preparing such cellular microcompartments.

15 Claims, 1 Drawing Sheet

(56) References Cited

OTHER PUBLICATIONS

Alessandri, K. et al. "A 3D printed microfluidic device for production of functionalized hydrogel microcapsules for culture and differentiation of human Neuronal Stem Cells (hNSC)" *Lab on a Chip*, 2016, pp. 1593-1604, vol. 16.
Ishihara, K. et al. "Reconstitution of a Patterned Neural Tube from Single Mouse Embryomc Stem Cells" *Organ Regeneration: 3D Stem Cell Culture & Manipulation, Methods in Molecular Biology*, 2017, pp. 43-55, vol. 1597.
Mansouri, V. et al. "Collagen-alginate microspheres as a 3D culture system for mouse embryonic stem cells differentiation to primordial germ cells" *Biologicals*, May 5, 2017, pp. 114-120, vol. 48.
Written Opinion in International Application No. PCT/FR2017/053225, dated Feb. 2, 2018, pp. 1-10.
Tabata, Y. et al. "Development of bioactive hydrogel capsules for the 3D expansion of pluripotent stem cells in bioreactors" *Biomaterials Science*, 2014, pp. 176-183, vol. 2.

\* cited by examiner

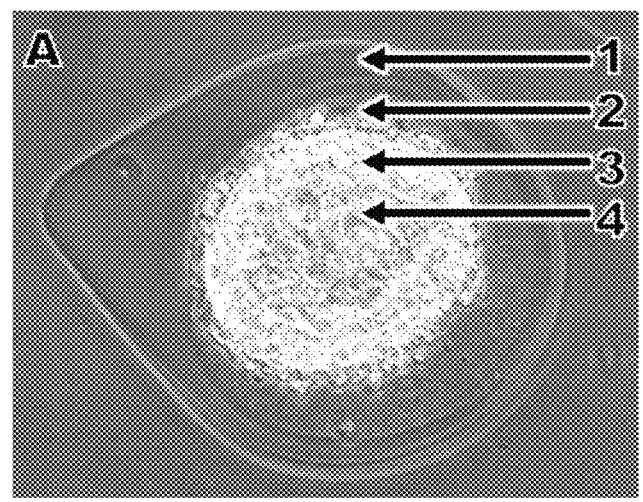
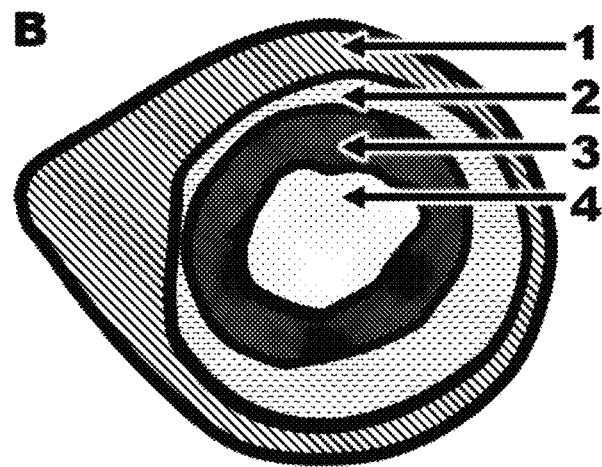

CELLULAR MICROCOMPARTMENT AND PREPARATION PROCESSES

CROSS-REFERENCE TO RELATED APPLICATION

This application is the U.S. national stage application of International Patent Application No. PCT/FR2017/053225, filed Nov. 23, 2017.

The invention relates to a cellular microcompartment allowing the pluripotency of human cells to be maintained. The invention also relates to a preparation process for obtaining such three-dimensional (3D) cell culture compartments.

Pluripotent cells are considered an important human cell resource, and their cultivation is of growing interest, particularly in the medical and pharmaceutical fields. Thus, producing pluripotent cells in large quantities would meet the new needs expressed by the pharmaceutical industry, which is reducing use of animal models in favor of cell models which are more relevant than the many cell lines currently in use. High throughput tests developed by pharmaceutical companies already use large quantities of human pluripotent cells. Similarly, tissue engineering and cell therapy in humans rely on the availability of industrial quantities of human pluripotent cells.

Currently, human pluripotent cells are usually cultured in a two-dimensional (2D) environment, such as on Petri dishes, very different from the 3D medium in which the cells normally evolve. The manipulation of these 2D cultured cells is often delicate, and requires in particular steps of purification, enzymatic detachment, etc. Furthermore, these cells are difficult to store and have a very low survival rate after freezing. However, the ability to use conventional carriers to send pluripotent cell cultures frozen in massive quantities, and compatible with liquid culture, represents a major challenge for both research laboratories and pharmaceutical industries.

In response to this situation, three-dimensional culture systems, which seek in particular to increase the throughput, efficiency and quality of human pluripotent stem cell culture systems, have been developed.

However, existing 3D culture systems are not entirely satisfactory. Uncontrolled fusion phenomena are often observed, resulting in cell aggregates whose size (>200 µm in diameter) makes the diffusion of the culture medium insufficient. Thus, within such 3D culture systems, cell differentiation is difficult to control and/or the cell death rate is very high. Generally, the lack of homogeneity of products derived from 3D cell culture and the cost of such techniques make this technology uncompetitive compared with 2D culture, which however is unsatisfactory.

There is thus a need for a 3D cell culture system that can provide large quantities of pluripotent cells with a controlled phenotype, which can be easily used both for basic research and industrially.

SUMMARY OF THE INVENTION

While working on the development of cellular microcompartments for 3D cell culture, the inventors developed a system that allows mass liquid suspension culture of human pluripotent cells while maintaining their phenotype. The developed microcompartments allow cells to be cultured in liquid medium, using the media conventionally used in 2D culture, while protecting the cells and controlling their phenotype to avoid wild-type differentiation and maintain pluripotency. More precisely, the microcompartments, or capsules, developed by the inventors comprise successively, organized in a substantially homocentric manner, a hydrogel shell, an extracellular matrix layer and one or more layers of human pluripotent cells surrounding a central lumen. The hydrogel shell of the capsules according to the invention, unlike existing culture systems, protects the cells from the mechanical stresses associated with collisions or fusions during liquid suspension culture. Particularly advantageously, the organization in "cysts" of the microcompartments according to the invention allows them to be frozen with a high cell survival rate. In addition, the cells can be differentiated before use, directly within the microcompartment, or used in the pluripotent stage, in both 3D and 2D culture. The inventors have also developed methods for preparing such cellular microcompartments, guaranteeing that the cyst form is obtained and maintained, which are suitable both for freezing and for controlling the phenotype of the cells they contain.

The subject-matter of the invention is therefore a cellular microcompartment comprising successively, organized around a lumen:
- at least one layer of human pluripotent cells;
- an extracellular matrix layer;
- an outer hydrogel layer.

Advantageously, culture medium fills the spaces left between the layers.

Another subject-matter of the invention is a process for preparing a cellular microcompartment according to the invention, comprising the steps consisting in
(a) incubating human pluripotent stem cells in a culture medium containing a RHO/ROCK pathway inhibitor;
(b) mixing the pluripotent stem cells from step (a) with an extracellular matrix;
(c) encapsulating the mixture from step (b) in a hydrogel layer;
(d) culturing the capsules obtained in step (c) in a culture medium containing a RHO/ROCK pathway inhibitor;
(e) rinsing the capsules from step (d) to remove the RHO/ROCK pathway inhibitor;
(f) culturing the capsules from step (e) for 3 to 20 days, preferentially 5 to 10 days, in a culture medium free of RHO/ROCK pathway inhibitor, and optionally recovering the cellular microcompartments obtained.

Another subject-matter of the invention is a process for preparing a cellular microcompartment according to the invention, comprising the steps consisting in
(a) mixing human differentiated cells with an extracellular matrix and cell reprogramming agents;
(b) encapsulating the mixture from step (a) in a hydrogel layer;
(c) culturing the capsules from step (b) for 10 to 40 days, and optionally recovering the cellular microcompartments obtained.

BRIEF DESCRIPTION OF THE FIGURES

FIG. 1: Photo (A) and schematic representation (B) of a cellular microcompartment forming a cyst according to the invention (1: hydrogel layer; 2: extracellular matrix layer; 3: layers of pluripotent cells; 4: lumen).

DETAILED DESCRIPTION

The subject-matter of the invention is a 3D cellular microcompartment comprising human pluripotent cells, in which the pluripotency of the cells is maintained.

Cellular Microcompartment

The cellular microcompartment according to the invention forms a cyst whose hollow center, or lumen, is preferentially aqueous. In the context of the invention, a "cyst" refers to a closed hollow structure containing substantially homocentric layers, in the sense that they are organized successively around the same point, the outer layer enveloping the matrix layer which envelops the cell layer, which surrounds the lumen. Generally, the pluripotent cells making up the cyst are polarized. The polarity of these cells within the cyst can be detected by the proteins TJP-1 or ZO-1, both located on the inner/apical side of the pluripotent cell layer adjacent to the lumen.

The lumen is generated, at the time of cyst formation, by the cells that multiply and develop on the extracellular matrix layer. Advantageously, the lumen contains a liquid and more particularly culture medium.

In the context of the invention, the "hydrogel layer" refers to a three-dimensional structure formed from a matrix of polymer chains swollen by a liquid, preferentially water. Advantageously, the hydrogel used is biocompatible, in the sense that it is not toxic to cells. Furthermore, the hydrogel layer must allow the diffusion of oxygen and nutrients to feed the cells contained in the microcompartment and allow them to survive. For example, the outer hydrogel layer contains alginate. Preferentially, the outer layer contains only alginate. In the context of the invention, "alginate" refers to linear polysaccharides formed from β-D-mannuronate (M) and α-L-guluronate (G), salts and derivatives thereof. Advantageously, the alginate is a sodium alginate, composed of more than 80% G and less than 20% M, with an average molecular mass of 100 to 400 KDa (e.g., PRONOVA® SLG100) and a total concentration comprised between 0.5% and 5% by mass. According to the invention, the hydrogel layer is cell-free. In one embodiment of the cellular microcompartment according to the invention, the outer layer comprises alginate.

In turn, the extracellular matrix layer may contain a few cells. Indeed, at the time of cyst formation, the cells create their space in the matrix and multiply, filling the microcompartment. The boundary between the extracellular matrix layer and the pluripotent cell layer may therefore not be perfectly clear. At the surface in contact with the cell layer, the extracellular matrix may thus contain a few pluripotent cells. Conversely, the surface of the extracellular matrix layer in contact with the hydrogel layer is cell-free.

The extracellular matrix layer is necessary for the survival of pluripotent cells in the microcompartment and for the creation of the cyst.

Preferentially, the extracellular matrix layer forms a gel on the inner side of the hydrogel layer, meaning the side directed towards the lumen of the microcompartment. The extracellular matrix layer comprises of a mixture of proteins and extracellular compounds necessary for cell culture, and more particularly the culture of pluripotent cells. Preferentially, the extracellular matrix comprises structural proteins, such as laminins containing α1, α4 or α5 subunits, β1 or β2 subunits, and γ1 or γ3 subunits, entactin, vitronectin, laminins, collagen, as well as growth factors such as TGF-beta and/or EGF. In one embodiment, the extracellular matrix layer consists of, or contains, Matrigel® and/or Geltrex®.

According to the invention, the cellular microcompartment contains one or more layers of human pluripotent stem cells. A pluripotent stem cell, or pluripotent cell, is a cell that has the ability to form all the tissues present in the whole original organism but cannot form a whole organism as such.

In a particular embodiment, the encapsulated cells are pluripotent stem cells, such as induced pluripotent stem (IPS) cells, multilineage-differentiating stress enduring (MUSE) cells found in the skin and bone marrow of adult mammals, or embryonic stem (ES) cells.

In the context of the invention, "induced pluripotent stem cells" (IPS cells) are defined as pluripotent stem cells obtained by genetic reprogramming of differentiated somatic cells and having a morphology and a potential for self-renewal and pluripotency partially similar to those of embryonic stem cells. These cells are notably positive for pluripotency markers, such as alkaline phosphatase staining and expression of the proteins NANOG, SOX2, OCT4 and SSEA3/4. The processes for obtaining induced pluripotent stem cells are well known to the skilled person and are notably described in articles by Yu et al. (Science, 2007, 318 (5858): 1917-1920), Takahashi et al. (Cell, 2007, 131 (5): 861-872) and Nakagawa et al. (Nat Biotechnol, 2008, 26 (1): 101-106).

In the case of embryonic stem cells, said pluripotent stem cells are cells derived from the internal cell mass of the blastocyst and which have the ability to lead to the formation of all tissues of the organism. The pluripotency of embryonic stem cells can be assessed by the presence of markers such as the transcription factors OCT4 and NANOG and surface markers such as SSEA3/4, Tra-1-60 and Tra-1-81. Embryonic stem cells can be obtained without destroying the embryo from which they originate, for example by using the technique described by Chung et al. (Cell Stem Cell, 2008, 2 (2): 113-117). In a particular embodiment, and for legal or ethical reasons, stem cells are defined as excluding human embryonic stem cells.

In one embodiment, the human pluripotent stem cells used for the microcompartments according to the invention are induced to pluripotency from somatic cells.

Advantageously, the cell layer contains at least 95% by volume, preferentially at least 96%, 97%, 98%, 99% of cells and of matrix produced by said cells. The cells are essentially pluripotent cells. "Essentially" means that at least 90% of the cells contained in the cell layer are pluripotent cells, preferentially at least 95%, 96%, 97%, 98%, 99%, 100%, are pluripotent cells.

Advantageously, the lumen of the cyst contains culture medium. In particular, any culture medium allowing the suspension culture of pluripotent cells may be used, and in particular any culture medium conventionally used in 2D culture.

Preferentially, the cellular microcompartment is closed. It is the outer hydrogel layer that gives the cellular microcompartment its size and shape. The microcompartment can have any shape compatible with cell encapsulation.

Advantageously, the dimensions of the cellular microcompartment are controlled. In one embodiment, the cellular microcompartment according to the invention has a spherical shape. Preferentially, the diameter of such a microcompartment is comprised between 10 μm and 1 mm, more preferentially between 50 μm and 500 μm, even more preferentially is less than 500 μm, preferably less than 400 μm.

In another embodiment, the cellular microcompartment according to the invention has an elongated shape. In particular, the microcompartment may have an ovoid or tubular shape. Advantageously, the smallest dimension of such an ovoid or tubular microcompartment is comprised between 10 µm and 1 mm, more preferentially between 50 µm and 500 µm, even more preferentially less than 500 µm, preferentially less than 400 µm. "Smallest dimension" means twice the minimum distance between a point on the outer surface of the hydrogel layer and the center of the microcompartment.

In a particular embodiment, the thickness of the outer hydrogel layer represents 5 to 40% of the radius of the microcompartment. The thickness of the extracellular matrix layer represents 5 to 80% of the radius of the microcompartment and is advantageously attached to the inner side of the hydrogel shell. The thickness of the pluripotent cell layer represents about 10% of the radius of the microcompartment. The pluripotent cell layer is in contact at least at one point with the extracellular matrix layer, a space filled with culture medium may be present between the matrix layer and the cyst. The lumen then represents 5 to 30% of the radius of the microcompartment. In the context of the invention, the "thickness" of a layer is the dimension of said layer extending radially relative to the center of the microcompartment.

In a particular example, the cellular microcompartment has a spherical shape with a radius of 100 µm. The hydrogel layer has a thickness of 5 µm to 40 µm. The extracellular matrix layer has a thickness of 5 µm to about 80 µm. The layer of pluripotent cells has a thickness of 10 to 30 µm, the lumen has a radius of 5 to 30 µm, roughly.

In general, the presence of the outer hydrogel layer imposes a maximum size on the cell layer and limits, by confinement, the uncontrolled proliferation of cells, which could lead to the anoxic death of the cells and/or uncontrolled differentiation of the cells in the deepest layers, meaning those closest to the lumen of the cyst. In 2D, on a Petri dish, the colonies are discs, the cells at the center of the disc tend to die (each new cell resulting from a division is excluded from the colony by the lack of space) or to differentiate under the constraints of the cells surrounding them, the cells on the edge tend to differentiate and only a band at the right distance has the optimal phenotype. The topology of the microcompartment presented here, the inner surface of the sphere formed by the capsule, makes it possible to generate a "colony" of stem cells (the pluripotent cell layer) "without edges" where all the cells are optimally and equally positioned both for the diffusion of small molecules and in terms of mechanical stresses. Advantageously, the cell density in the microcompartment is comprised between 1 and several thousand cells per microcompartment, preferably between 50 and 1000 cells per 100 µm radius microcompartment.

Processes for Preparing Cellular Microcompartments

The invention also relates to processes for preparing cellular microcompartments which make it possible to obtain the cellular microcompartment according to the invention. More specifically, the invention proposes to produce cellular microcompartments containing pluripotent stem cells organized into cysts directly from pluripotent stem cells, or from differentiated cells which will be reprogrammed into pluripotent cells inside the hydrogel capsule during the formation of the microcompartments.

Any method for producing cellular microcompartments containing extracellular matrix and pluripotent stem cells within a hydrogel capsule may be used for the implementation of the preparation process according to the invention. In particular, it is possible to prepare microcompartments by adapting the microfluidic method and device described in Alessandri et al., 2016 ("A 3D printed microfluidic device for production of functionalized hydrogel microcapsules for culture and differentiation of human Neuronal Stem Cells (hNSC)", Lab on a Chip, 2016, vol. 16, no. 9, p. 1593-1604), in accordance with the steps described below.

In a first embodiment, the preparation process according to the invention comprises the steps consisting in
  (a) incubating human pluripotent stem cells in a culture medium containing a RHO/ROCK pathway inhibitor;
  (b) mixing the pluripotent stem cells from step (a) with an extracellular matrix;
  (c) encapsulating the mixture from step (b) in a hydrogel layer;
  (d) culturing the capsules obtained in step (c) in a culture medium containing a RHO/ROCK pathway inhibitor;
  (e) rinsing the capsules from step (d) to remove the RHO/ROCK pathway inhibitor;
  (f) culturing the capsules from step (e) for 3 to 20 days, preferentially 5 to 10 days, until a cyst is obtained, and optionally recovering the cellular microcompartments obtained.

Incubation step (a) and culture step (d) in a medium containing one or more RHO/ROCK ("Rho-associated protein kinase") pathway inhibitors, such as thiazovivin ($C_{15}H_{13}N_5OS$) and/or Y-27632 ($C_{14}H_{21}N_3O$), promote the survival of pluripotent stem cells and cell adherence to the extracellular matrix when the outer hydrogel layer is formed around said extracellular matrix. It is however desirable that these steps be limited in time, so that RHO/ROCK pathway inhibitors do not prevent the formation of cysts.

Thus, preferentially, the incubation of step (a) is conducted for a time comprised between a few minutes and a few hours, preferably between 2 minutes and 2 hours, more preferably between 10 minutes and 1 hour.

Similarly, preferentially, culture step (d) is conducted for a time comprised between 2 and 48 hours, preferably for a time comprised between 6 and 24 hours, more preferentially for a time comprised between 12 and 18 hours.

Step (e) is necessary to ensure the removal of all traces of RHO/ROCK pathway inhibitors. Step (e) is carried out, for example, by rinsing, and preferably by several rinses, in successive culture media free of RHO/ROCK pathway inhibitors.

Advantageously, step (f) is conducted for a sufficient time to obtain a cellular microcompartment in which the pluripotent cell layer and the lumen have a cumulative thickness equal to 10 to 95% of the radius of the microcompartment, that is to say, for a sufficient time to allow to pass from two cells to about a thousand cells. Any culture medium suitable for pluripotent stem cell culture may be used, and notably saline phosphate buffer such as Roswell Park Memorial Institute medium.

In one embodiment, the process according to the invention comprises an intermediate step (a') consisting in dissociating the pluripotent stem cells from step (a) before step (b), preferentially by means of an enzyme-free reagent. Advantageously, said reagent is inhibited or rinsed before the encapsulation step, in particular by successive rinses in a specific medium for pluripotent cells. For example, the reagent used is an iso-osmotic buffer containing EDTA or EGTA such as ReLeSR®. Of course, it is also possible to use trypsin or a reagent containing an enzyme, but the survival rate of pluripotent cells at the end of this step may then be lower compared with the use of an enzyme-free reagent. In all cases, the rinsing step is necessary to remove any trace of the reagent used for cell dissociation.

In one embodiment, at least one of steps (a'), (b), (c), (d) or (e) is performed at a temperature comprised between 0 and 8° C., preferentially all of steps (a'), (b), (c), (d) and (e). Maintaining a temperature substantially equal to 4° C. allows the biological processes of the cells to become dormant, including the transduction of signals from the external environment. This makes it possible to limit the phenomenon of cell death, which could be induced by cell detachment.

In another embodiment, the process for preparing a cellular microcompartment according to the invention comprises the steps consisting in
(a) mixing differentiated human cells with an extracellular matrix and cell reprogramming agents that do not permeate the hydrogel layer;
(b) encapsulating the mixture from step (a) in a hydrogel layer;
(c) culturing the capsules from step (b) for 10 to 40 days, and optionally recovering the cellular microcompartments obtained.

In another embodiment, the process for preparing a cellular microcompartment according to the invention comprises the steps consisting in
(a) mixing differentiated human cells with an extracellular matrix;
(b) encapsulating the mixture from step (a) in a hydrogel layer;
(c) incubating the capsules from step (b) with cellular reprogramming agents that permeate the hydrogel layer and culturing the capsules for 10 to 40 days, and optionally recovering the cellular microcompartments obtained.

For example, the differentiated cells used are fibroblasts.

The skilled person knows how to reprogram a differentiated cell into a stem cell by reactivating the expression of genes associated with the embryonic stage by means of specific factors, referred to in the present invention as "reprogramming agents". Examples include the methods described in Takahashi et al., 2006 ("Induction of pluripotent stem cells from mouse embryonic and adult fibroblast cultures by defined factors" Cell, 2006 Vol 126, pages 663-676), Ban et al., 2009 ("Efficient induction of transgene-free human pluripotent stem cells using a vector based on Sendai virus, an RNA virus that does not integrate into the host genome" Proc Jpn Acad Ser B Phys Biol Sci. 2009; 85 (8):348-62) and in international application WO2010/105311 entitled "Production of reprogrammed pluripotent cells".

The reprogramming agents are advantageously co-encapsulated with the differentiated cells, so as to concentrate the product and promote contact with all the cells. In the case of reprogramming agents that permeate the hydrogel layer, it is possible to add said agents to the culture medium after the encapsulation step.

The reprogramming agents make it possible to impose on the cells a succession of phenotypic changes up to the pluripotent stage. Advantageously, reprogramming step (a) is performed using specific culture media, promoting these phenotypic changes. For example, the cells are cultured in a first medium comprising 10% human or bovine serum, in Eagle's minimal essential medium (DMEM) supplemented with a serine/threonine protein kinase receptor inhibitor (such as the product SB-431542 ($C_{22}H_{16}N_4O_3$)), one or more RHO/ROCK ("Rho-associated protein kinase") pathway inhibitors such as thiazovivin and/or Y-27632, fibroblast growth factors such as FGF-2, ascorbic acid, and antibiotics such as Trichostatin A ($C_{17}H_{22}N_2O_3$). Then the culture medium is replaced by medium that promotes the multiplication of pluripotent cells, such as mTeSR®1.

Advantageously, the capsules from step (b) each contain between 1 and 500 differentiated cells, preferentially between 50 and 200.

In one embodiment, at least one of steps (a), (b), (c) or (d) is performed at a temperature comprised between 0 and 4° C., preferentially all of steps (a), (b), (c) and (d). Maintaining a temperature of 4° C. or lower allows the biological processes of the cells to become dormant, including the transduction of signals from the external environment. This makes it possible to limit the phenomenon of cell death, which could be induced by cell detachment.

The microcompartments obtained during step (d) can be sorted so as to isolate the cellular microcompartments with the desired cyst form. Such a sorting step can be carried out continuously, so as to separate the cellular microcompartments already having the desired cyst form from the microcompartments still being formed. Such a sorting step can be done by simple morphological analysis, without disturbing the other microcompartments in which reprogramming is still in progress and/or the cyst organization not yet completed.

In general, the cellular microcompartments obtained by the processes of the invention may then be frozen before use. Indeed, the cyst form promotes cell survival within the microcompartment, and after thawing, the survival rate is greater than 80%. Advantageously, freezing is carried out using liquid nitrogen to quickly vitrify the microcompartments and limit the risk of crystal formation within the lipid membranes of the cells. The cellular microcompartments may be suspended in a freezing buffer that promotes cell survival. For example, it is possible to use the freezing buffers conventionally used to freeze embryos.

The cellular microcompartments, thus frozen, may then be thawed as needed.

Applications

The cellular microcompartments concerned by the present invention can be used for many applications. Indeed, the cells they contain can be easily recovered by simple hydrolysis and/or dissolution of the outer hydrogel layer. Furthermore, it is possible to differentiate pluripotent cells within the hydrogel capsule or after hydrolysis/dissolution of said hydrogel capsule, as needed, in order to obtain large quantities of cell lines of interest. Advantageously, the cells are differentiated into one or more cell types of interest, within the microcompartment, meaning before hydrolysis of the outer hydrogel layer.

The cellular microcompartments, and more precisely the cells they contain, can be used for research and development purposes, both in the form of a 3D cell network and more conventionally in 2D culture. They can also be used for therapeutic purposes, such as cell therapy, tissue engineering, etc.

EXAMPLES

Example 1

Protocol for Obtaining Cellular Microcompartments from Human Cells Induced to Pluripotency Solutions Used Solution 1, DMEMF12 medium base supplemented with 2 µM Thiazovivin Solution 2, PBS without magnesium and without calcium supplemented with 1 µM 2 µM Thiazovivin Solution 3, non-enzymatic cell detachment buffer: RelesR™ supplemented with 2 µM Thiazovivin.

Solution 4, pluripotent stem cell culture medium: MTeSR1™ hES/hIPS cell medium STEMCELL™).

Solution 4+, Solution 4 supplemented with 2 µM Thiazovivin.

Solution 5, Matrigel™.

Solution 6, 300 mM sorbitol with 2 µM Thiazovivin.

Cell Solution

A 25 $cm^2$ Petri dish of human IPS cells (obtained from Primary Dermal Fibroblast; Normal, Human, Adult ATCC® PCS-201-012™ and CytoTune™-iPS 2.0 Sendai Reprogramming Kit (item number A16517) using the technology shown in example 2) at 90% confluence is then used to match the recommended volumes. All the following steps are carried out at 4° C. until the hydrogel shell is crosslinked in the calcium bath.

Step 1: Rinse the cells with solution 1. Wait 10 minutes to 1 hour.

Step 2: Rinse twice with 4 mL of solution 2.

Step 3: Gently aspirate the solution.

Step 4: Incubate the cells with 4 mL of solution 3 for 5-10 minutes.

Step 5: Detach the cells with 2 mL of solution 4+ with a wide-tipped pipette to reduce shear stress.

Step 6: Centrifuge the cell suspension at 360 g for 5 minutes.

Step 7: Aspirate the supernatant.

Step 8: Resuspend with 0.5 mL of solution 4+.

Step 9: Centrifuge again at 360 g and aspirate the supernatant.

Step 10: Resuspend the cell pellet in 70 µL of solution 5 and 100 µL of solution 6 (the volume of the pellet should be 30 The cell solution is ready.

Encapsulation

The encapsulation device is prepared as described in Alessandri et al., 2016 ("A 3D printed microfluidic device for production of functionalized hydrogel microcapsules for culture and differentiation of human Neuronal Stem Cells (hNSC)", Lab on a Chip, 2016, vol. 16, no. 9, pp. 1593-1604).

In summary, the different parts of the device are sterilized (by autoclave); the three necessary solutions are loaded on three syringe pumps, i) alginate solution (PRONOVA®SLG100 at 2% by mass in distilled water), ii) intermediate solution (300 mM sorbitol), iii) cell solution (prepared in the previous step); the three solutions are co-injected concentrically using a microfluidic injector which forms a jet that breaks down into drops whose outer layer is the alginate solution and the core the cell solution; these drops are collected in a calcium bath (at 100 mM) that stiffens the alginate solution to form the shell.

To improve the monodispersity of the cellular microcompartments, the alginate was charged with a +2 kV DC current. A mass ring of 2 cm in diameter is placed 500 µm from the tip in the plane perpendicular to the axis of the jet leaving the microfluidic injector to generate the electric field.

It should be noted that under these encapsulation conditions, the Matrigel® layer forms spontaneously.

Treatment after Encapsulation:

Step 1: The capsules are collected with a 40 µm cell sieve and then after rinsing with solution 1 they are stored in a 75 $cm^2$ flask with 20 mL of solution 4+.

Step 2: The flask is kept for 12 h in the incubator at 37° C. and 5% $CO_2$.

Step 3: Change the medium for solution 4 to allow the formation of cysts.

Step 4: After 24 to 72 hours, cysts of a few dozen cells are formed in the capsules. The cellular microcompartments are mature after 5 to 10 days.

Example 2

Protocol for Obtaining Cellular Microcompartments from Human Fibroblasts

Solutions Used:

Solution 1, DMEMF12 medium base

Solution 2, PBS without magnesium without added calcium

Solution 3, trypsin EDTA cell detachment buffer

Solution 4, fibroblast culture medium: 10% human serum in a DMEM medium base

Solution 4+, Solution 4 supplemented with 2 µM Thiazovivin.

Solution 5, Matrigel™

Solution 6, 300 mM sorbitol with 2 µM Thiazovivin.

Cell Solution:

A 25 $cm^2$ Petri dish of human fibroblasts (Primary Dermal Fibroblast; Normal, Human, Adult (ATCC® PCS-201-012®) with low confluence density is then used to match the recommended volumes (1 to 2 million cells). All the following steps are carried out at 4° C. until the shell is crosslinked in the calcium bath.

Step 1: Rinse the cells with solution 2.

Step 2: Gently aspirate the solution.

Step 3: Incubate the cells with 4 mL of solution 3 for 5-10 minutes.

Step 4: Detach the cells with 2 mL of solution 4+ with a wide-tipped pipette to reduce shear stress.

Step 6: Centrifuge the cell suspension at 360 g for 5 minutes.

Step 7: Aspirate the supernatant.

Step 8: Resuspend with 0.5 mL of solution 4+.

Step 9: Centrifuge again at 360 g and aspirate the supernatant.

Step 10: Resuspend the cell pellet in 90 µL of solution 5 and 100 µL of solution 6 (the pellet volume should be 10 µL).

Step 11: Add ⅒ of the contents of the "CytoTune®-IPS 2.0 Sendai Reprogramming Kit" (containing a reprogramming virus) provided for a 6-well plate. The cell solution is ready.

Encapsulation: The encapsulation is performed in accordance with the protocol of example 1.

Treatment after Encapsulation:

Step 1: The capsules are collected with a 40 µm cell sieve and then after rinsing with solution 1 they are stored in a 75 $cm^2$ flask with 20 mL of solution 4+.

Step 2: The flask is kept for 24 h in the incubator at 37° C. and 5% $CO_2$.

Step 3: Change the medium every day. Each capsule contains 1 to 10 fibroblasts at capsule formation. The reprogramming virus has a transformation efficiency of about 0.2%. Most of the capsules will therefore contain very few reprogrammed cells, if any. Cysts begin to form after 15 to 40 days. The fibroblasts have an elongated shape and do not form cysts. Thus, all the cysts that are formed are formed of IPS cells.

The invention claimed is:

1. A cellular microcompartment, wherein the cellular microcompartment is a cyst comprising a central lumen and the following successively arranged homocentric layers: at least one layer of human pluripotent cells, an extracellular matrix layer, and an outer hydrogel layer, the lumen being hollow and surrounded by human pluripotent cells deposited on or in said extracellular matrix, wherein the human pluripotent cells are polarized and wherein the cell density is between one and several thousand cells per microcompartment, wherein the cellular microcompartment maintains the central lumen after 5 days in culture.

2. The cellular microcompartment according to claim 1, wherein said microcompartment is closed.

3. The cellular microcompartment according to claim 1, wherein the outer layer comprises alginate.

4. The cellular microcompartment according to claim 1, wherein said microcompartment has a spherical or elongated shape.

5. The cellular microcompartment according to claim 1, wherein said microcompartment has a diameter or a smallest dimension between 10 μm and 1 mm.

6. A process for preparing a cellular microcompartment wherein the cellular microcompartment is a cyst, the method comprising:
   (a) incubating human pluripotent stem cells in a culture medium containing a RHO/ROCK pathway inhibitor;
   (b) mixing the pluripotent stem cells from step (a) with an extracellular matrix;
   (c) encapsulating the mixture from step (b) in a hydrogel layer;
   (d) culturing the capsules obtained in step (c) in a culture medium containing a RHO/ROCK pathway inhibitor;
   (e) rinsing the capsules from step (d) to remove the RHO/ROCK pathway inhibitor;
   (f) culturing the capsules from step (e) for 5 to 20 days to form a cellular microcompartment comprising a lumen and the following successively arranged homocentric layers: at least one layer of human pluripotent cells, an extracellular matrix layer, and an outer hydrogel layer, the lumen being hollow and formed by human pluripotent cells deposited on or in said extracellular matrix and, optionally, recovering the cellular microcompartments, wherein the cellular microcompartment maintains the central lumen after 5 days in culture.

7. The process for preparing a microcompartment according to claim 6, comprising an intermediate step of dissociating the pluripotent stem cells from step (a) before step (b).

8. The process for preparing a microcompartment according to claim 7, wherein the pluripotent stem cells are dissociated by an enzyme free reagent.

9. A process for preparing a cellular microcompartment according to claim 1 comprising:
   (a) mixing human differentiated cells with an extracellular matrix and cell reprogramming agents;
   (b) encapsulating the mixture from step (a) in a hydrogel layer;
   (c) culturing the capsules from step (b) for 10 to 40 days to form a cellular microcompartment comprising a lumen and the following successively arranged homocentric layers: at least one layer of human pluripotent cells, an extracellular matrix layer, and an outer hydrogel layer, the lumen being hollow and formed by human pluripotent cells deposited on or in said extracellular matrix, and optionally recovering the cellular microcompartments obtained, wherein the cellular microcompartment maintains the central lumen after 5 days in culture.

10. The process for preparing a cellular microcompartment according to claim 9, wherein each capsule from step (b) contains between 1 and 500 differentiated cells.

11. The process for preparing a cellular microcompartment according to claim 6, said method comprising a subsequent step of freezing the cellular microcompartments.

12. The process for preparing a cellular microcompartment according to claim 7, said method comprising a subsequent step of freezing the cellular microcompartments.

13. The process for preparing a cellular microcompartment according claim 8, said method comprising a subsequent step of freezing the cellular microcompartments.

14. The process for preparing a cellular microcompartment according to claim 9, said method comprising a subsequent step of freezing the cellular microcompartments.

15. The process for preparing a cellular microcompartment according to claim 10, said method comprising a subsequent step of freezing the cellular microcompartments.

* * * * *